(12) United States Patent
Michel et al.

(10) Patent No.: US 8,764,807 B2
(45) Date of Patent: Jul. 1, 2014

(54) CALCANEUS STEP PLATE

(75) Inventors: Gerlinde Michel, Munich (DE); C. Niek van Dijk, Abcoude (NL)

(73) Assignee: Arthrex, Inc., Naples, FL (US)

( * ) Notice: Subject to any disclaimer, the term of this patent is extended or adjusted under 35 U.S.C. 154(b) by 450 days.

(21) Appl. No.: 13/154,805

(22) Filed: Jun. 7, 2011

(65) Prior Publication Data

US 2011/0306977 A1 Dec. 15, 2011

Related U.S. Application Data

(60) Provisional application No. 61/353,590, filed on Jun. 10, 2010.

(51) Int. Cl.
*A61B 17/80* (2006.01)

(52) U.S. Cl.
USPC .......................................... 606/280; 606/281

(58) Field of Classification Search
USPC ............. 606/71, 70, 280–289, 293, 297–299; 623/18.11, 21.18
See application file for complete search history.

(56) References Cited

U.S. PATENT DOCUMENTS

| 4,120,298 | A | | 10/1978 | Fixel |
| 4,479,491 | A | * | 10/1984 | Martin .......................... 606/279 |
| 4,800,874 | A | | 1/1989 | David et al. |
| 5,364,399 | A | | 11/1994 | Lowery et al. |
| 5,487,741 | A | * | 1/1996 | Maruyama et al. ............. 606/60 |
| 6,235,032 | B1 | * | 5/2001 | Link .............................. 606/280 |
| 7,189,237 | B2 | * | 3/2007 | Huebner ........................ 606/291 |
| 8,080,010 | B2 | * | 12/2011 | Schulz et al. ................... 606/70 |
| 8,105,366 | B2 | * | 1/2012 | Null et al. ...................... 606/280 |
| 8,425,515 | B2 | * | 4/2013 | Gamache et al. ............... 606/70 |
| 2005/0251138 | A1 | | 11/2005 | Boris et al. |
| 2007/0073297 | A1 | | 3/2007 | Reynolds |
| 2010/0121325 | A1 | | 5/2010 | Tyber et al. |
| 2010/0217327 | A1 | | 8/2010 | Vancelette et al. |

* cited by examiner

*Primary Examiner* — Anu Ramana
*Assistant Examiner* — Michael Araj
(74) *Attorney, Agent, or Firm* — Dickstein Shapiro LLP (57) ABSTRACT

A calcaneus plate provided with two vertically-spaced plate sections, with corner-located screw holes. An intermediate wall connects the plate sections. An arcuate protrusion extends from the intermediate wall and contains an internal sliding mechanism for a compression screw. The sliding mechanism includes an arc-shaped compression hole with an elongated opening that includes a ridge upon with the compression screw head can slide.

15 Claims, 13 Drawing Sheets

CALCANEUS STEP PLATE

CROSS-REFERENCE TO RELATED APPLICATIONS

This application claims the benefit of U.S. Provisional Application No. 61/353,590, filed Jun. 10, 2010, the entire disclosure of which is incorporated by reference herein.

FIELD OF THE INVENTION

The present invention relates to a novel bone plate for calcaneal fracture treatment.

BACKGROUND OF THE INVENTION

Calcaneal fractures are typically caused by a high-velocity impact to the heel (for example, a fall from a height of at least two meters or an impact as a result of a motor vehicle accident). Calcaneal fractures may be extra or intra-articular.

One method currently used for treatment of calcaneal fractures is surgical treatment with open reduction and internal fixation, to restore the articular surface of the calcaneus and to obtain an anatomic reconstruction (height and width of the calcaneus). Although open reduction and internal fixation of intra-articular calcaneal fractures has become a standard surgical procedure with relatively low complication rate, there are still problems associated with this technique, primarily because of the complicated physical arrangement of the articular surfaces of the calcaneus (calcaneal bone). Clinical and technical problems can also occur due to the thickness and the stiffness of the plates, in particular superficial necrosis of the surgical wounds and peroneal tendonitis. These problems are related to the traction onto the skin flap during surgery and to the thickness of the plates that may cause ischemic problems to the skin and impingement of the peroneal tendons.

In addition, most plates have a limited number of holes and do not allow for significant molding because of their thickness. In this situation, the screws have to be inserted in predetermined sites of the calcaneal wall, and especially in the fractured zones of the lateral calcaneal wall, in the small fractures. Sometimes, this can lead to insufficient grip of the screws and therefore insufficient mechanical resistance of the implant. In those circumstances, early movement to prevent joint stiffness and enhance fractured soft tissue healing is not possible.

Accordingly, there is a need for better compression and load distribution between the articular surfaces of a fractured calcaneus, with increased stability by locking screw fixation and bridging of the fracture line. A plate with a step configuration that confers improved remodeling according to the lateral wall of the calcaneus and that is suited to the mechanical and biological characteristics of the method (open reduction and internal fixation) of intra-articular calcaneal fractures, with improved results, is also needed. A calcaneus correction osteotomy plate that reduces irritation of soft tissues and tendons, and decreases the number of late complications necessitating corrective procedures occurring subsequent to the fracture treatment, is also needed.

SUMMARY OF THE INVENTION

The present invention provides a calcaneus plate (a correction osteotomy plate) provided with two vertically-spaced plate sections, with corner-located screw holes. An intermediate wall connects the plate sections. An arc-shaped (arcuate) protrusion extends from the intermediate wall and contains an internal sliding mechanism for a compression screw. The sliding mechanism includes an arc-shaped compression hole with an elongated opening that includes a ridge upon with the compression screw head can slide.

The arc-shaped compression hole provides a unique sliding mechanism that imparts compression on the counter cortex and helps with the sliding osteotomy as the tendons tend to pull back. The center sliding mechanism of the step plate of the invention also allows tilting of the compression screw (with both sliding and rotation of the compression screw) to achieve compression on the counter cortex.

Other features and advantages of the present invention will become apparent from the following description of the invention, which refers to the accompanying drawings.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides a bone plate (a correction osteotomy plate) that may be used in conjunction with various calcaneal repair procedures.

The calcaneus step plate of the present invention has a stepped configuration and is provided with two vertically-spaced plate sections connected by an intermediate wall having a center sliding mechanism. The two vertically-spaced plate sections are about parallel to each other and the intermediate wall extends about perpendicular to them. The two vertically-spaced plate sections extend on opposite sides of the intermediate wall and are symmetrically positioned relative to the intermediate wall.

Each of the two vertically spaced plate sections is provided with corner-located screw holes. The corner-located screw holes are preferably not configured to function as slide holes.

An arc-shaped (arcuate) protrusion extends away from the intermediate wall. The arc-shaped (arcuate) protrusion may be attached to, or integral with, the intermediate wall. The arc-shaped (arcuate) protrusion contains an internal, truncated passageway (an arc-shaped compression hole) for a compression screw. The truncated passage includes an inner outlet opening smaller in cross-section than its outer, elongated inlet opening. The outer, elongated opening includes a ridge upon which the head of the compression screw can slide.

The arc-shaped compression hole formed within the arcuate protrusion provides a unique center sliding mechanism that imparts compression on the counter cortex and helps with the sliding osteotomy as the tendons tend to pull back. The center sliding mechanism of the step plate of the invention also allows sliding of the screw in the middle (for both sliding and rotation of the compression screw) to achieve compression on the counter cortex.

Referring now to the drawings, where like elements are designated by like reference numerals, FIGS. 1-5 illustrate various perspective views of calcaneus step plate 100 that may be employed for calcaneal fracture repairs.

Calcaneus step plate 100 of the present invention is provided with two vertically-spaced plate sections 10, 20 connected by an intermediate wall 30 having a unique center sliding mechanism. The two vertically-spaced plate sections 10, 20 are about parallel to each other and the intermediate wall 30 extends about perpendicular to each of the plate sections 10, 20 (with plate sections 10, 20 extending on opposite sides of the intermediate wall 30).

Each of the two vertically spaced plate sections 10, 20 is provided with corner-located holes 15 (configured to accommodate fixation devices such as screws 16). The corner-located holes 15 are preferably not configured to function as slide holes.

Figure 1:
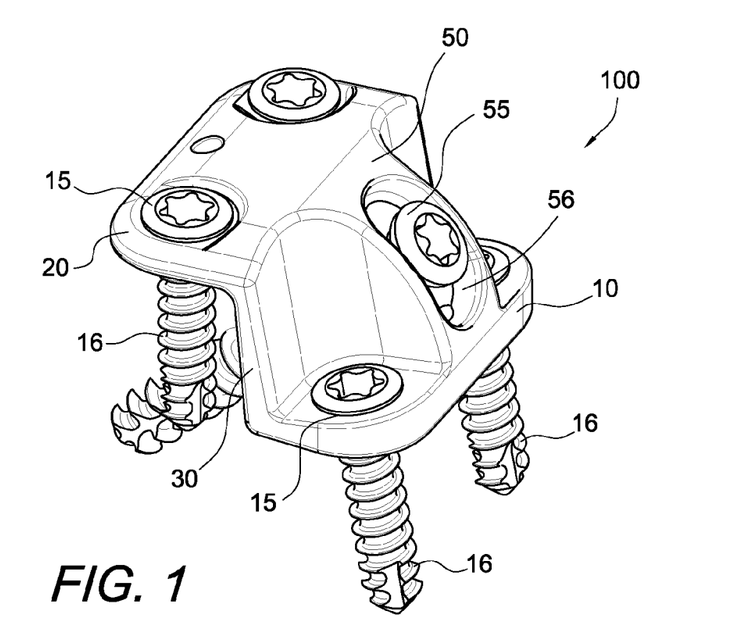
FIGS. 1-5 illustrate various views of a calcaneal step (correction osteotomy) plate of the present invention.
Figure 2:
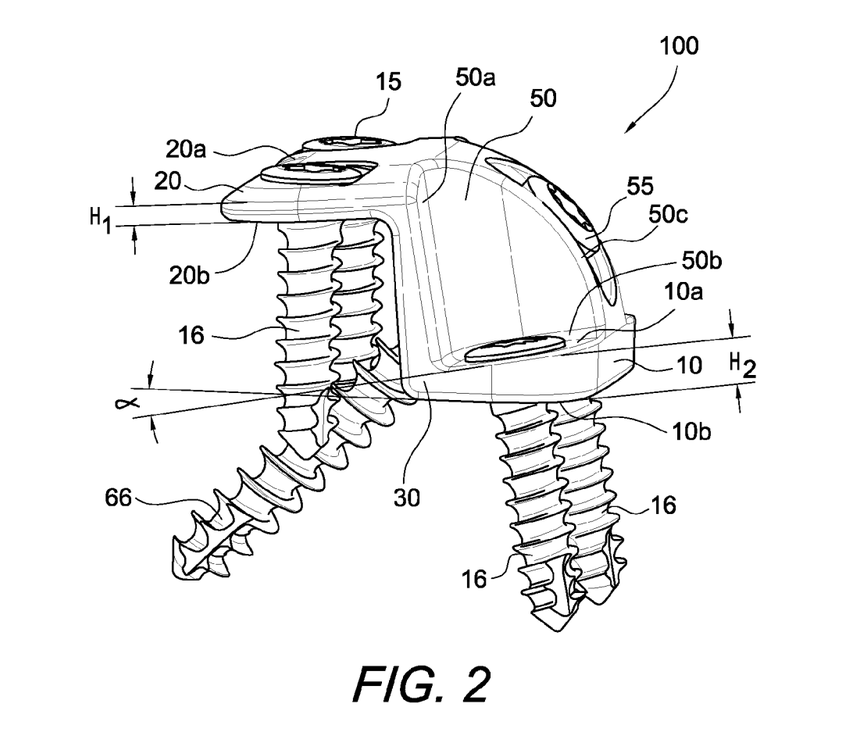
Figure 3:
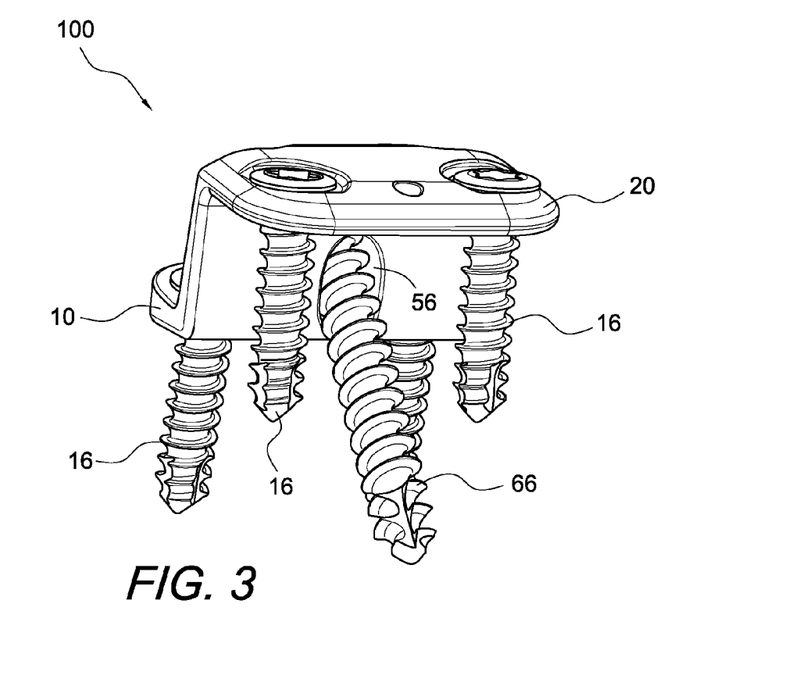
Figure 4:
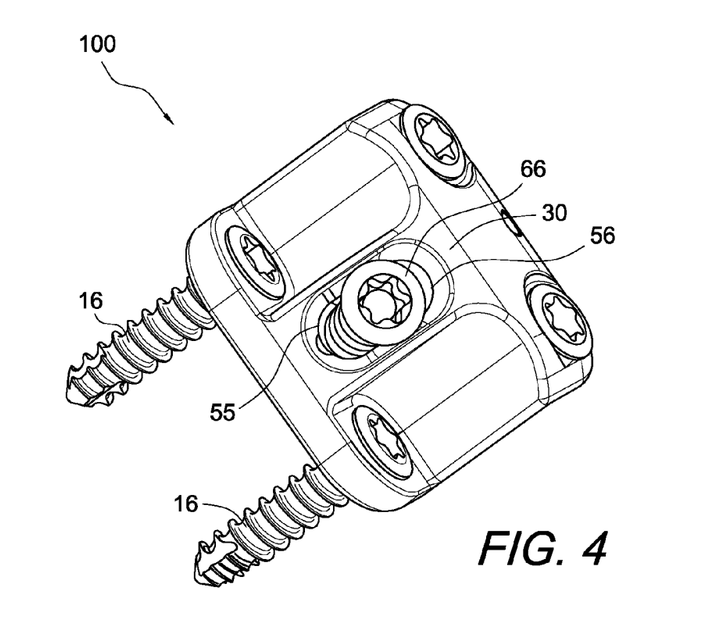
Figure 5:
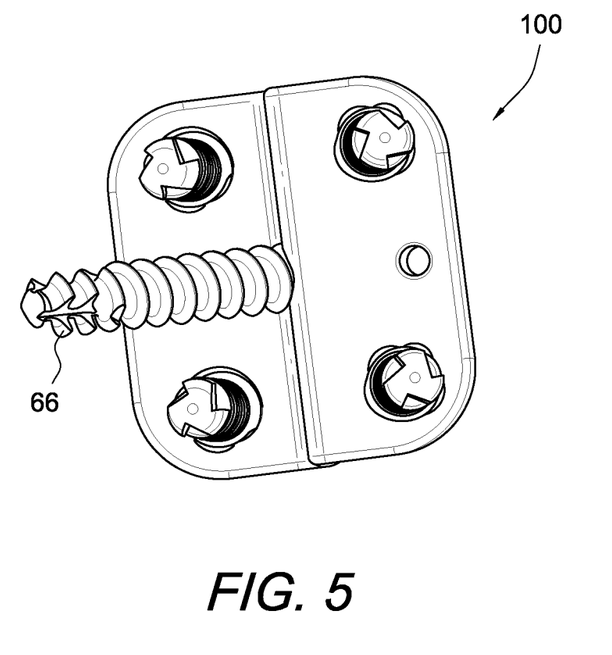

In an exemplary embodiment only, one of the two plate sections 10, 20 (for example, plate section 10 of FIG. 2) of the plate 100 has a wedged design as opposed to the parallel design of the other of the two plate sections (for example, plate section 20 of FIG. 2). An upper (top) surface 10a of the plate section 10 extends in a direction non-parallel to a lower (bottom) surface 10b, forming an angle α of about 5 to about 45 degrees. The other plate section 20 has an upper (top) surface 20a which extends in a direction about parallel to a lower (bottom) surface 20b. In other words, and as shown in FIG. 2, one of the first and second plate sections 10, 20 (for example, plate section 20) has a uniform height H1 and the other one of the first and second plate sections 10, 20 (for example, plate section 10) has a non-uniform (gradual) height H2 with a wedged profile. The special profile of the plate section 10 enables orthograde placement of the fixation device (for example, a screw) even in the case of angled bone surfaces.

An arc-shaped (arcuate) protrusion 50 extends from the intermediate wall 30 and contains an internal sliding mechanism 55 for a compression screw 66. The arcuate protrusion 50 is bound by two straight walls 50a, 50b, connected by an arcuate wall 50c (as shown in FIG. 2) which abuts sliding mechanism 55. The sliding mechanism 55 includes an arc-shaped compression hole 56 with an elongated opening that includes a ridge upon with the head of the compression screw 66 can slide (as detailed below with reference to FIGS. 6-25).

The arc-shaped compression hole 56 provides a unique sliding mechanism that imparts compression on the counter cortex and helps with the sliding osteotomy as the tendons tend to pull back. The center sliding mechanism 55 of the step plate of the invention also allows tilting of the compression screw 66 (with both sliding and rotation of the compression screw 66) to achieve compression on the counter cortex.

Calcaneus step plate 100 of the present invention is preferably formed of a metal such as titanium, titanium alloy, stainless steel, or other materials that possess mechanical and physical properties suitable for coupling bones together. Preferably, the grain of the metal is oriented parallel with the longer dimension of the bone plate. Calcaneus step plate 100 of the present invention can be provided in various sizes depending on the anatomical size of the calcaneus to be treated.

FIGS. 6-17 illustrate an exemplary sequence of steps of a calcaneal fracture treatment (undergoing the medial shift approach) with the calcaneal step plate 100 of the present invention, and according to one embodiment of the present invention. FIGS. 18-25 illustrate an exemplary sequence of steps of a calcaneal fracture treatment (the lateral shift approach) with the calcaneal step plate 100 of the present invention, and according to another embodiment of the present invention.

FIGS. 6-17 (Medial Shift)

Figure 6:
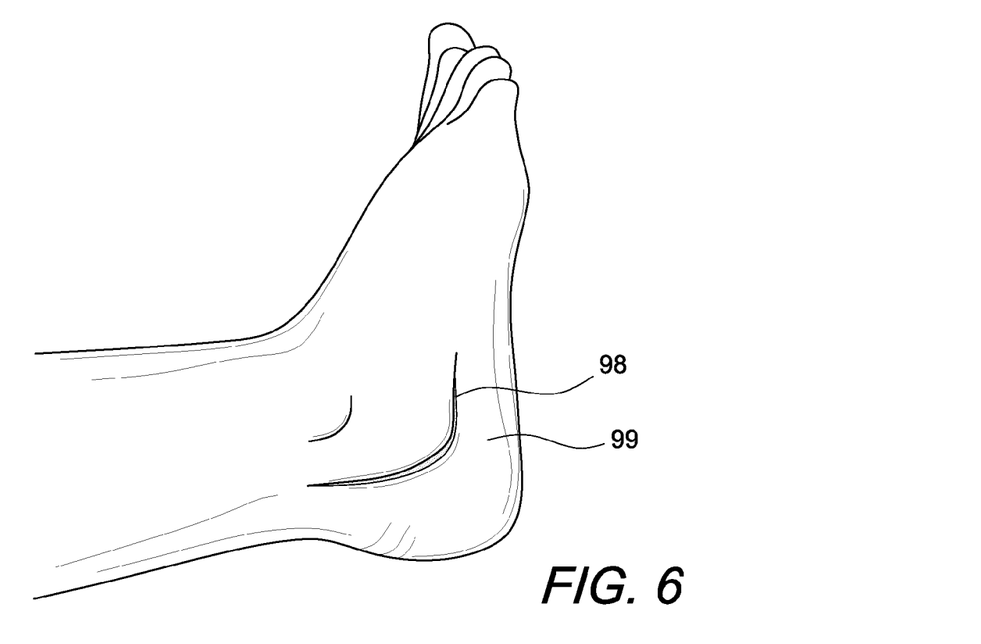
FIGS. 6-17 illustrate a sequence of steps of a calcaneal fracture treatment (medial shift approach) with the correction osteotomy plate of the present invention.
Figure 7:
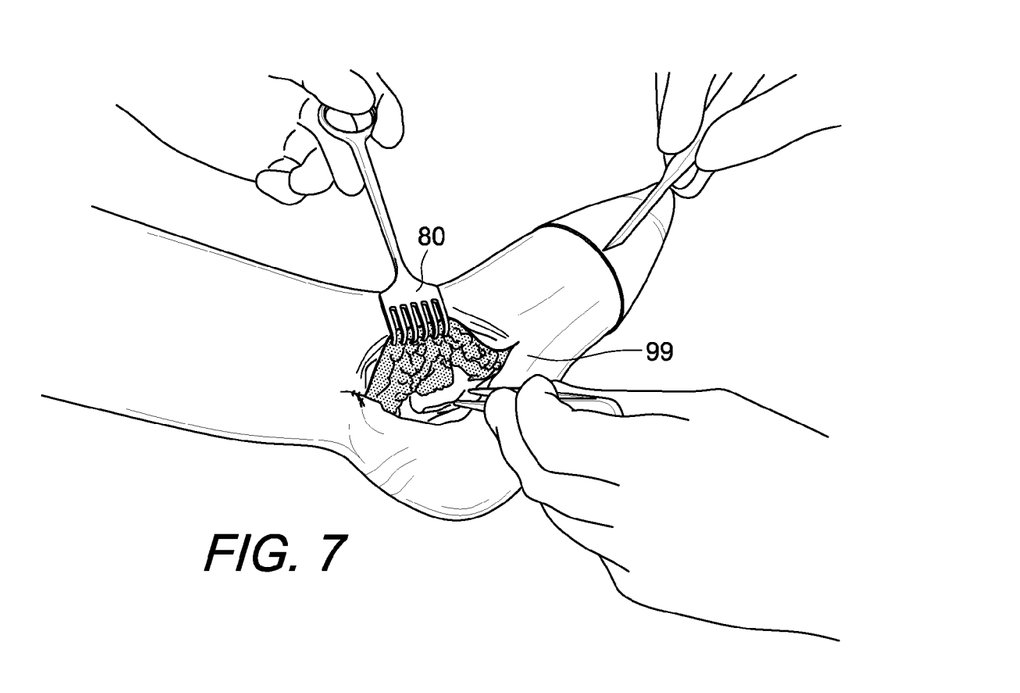
Figure 7A:
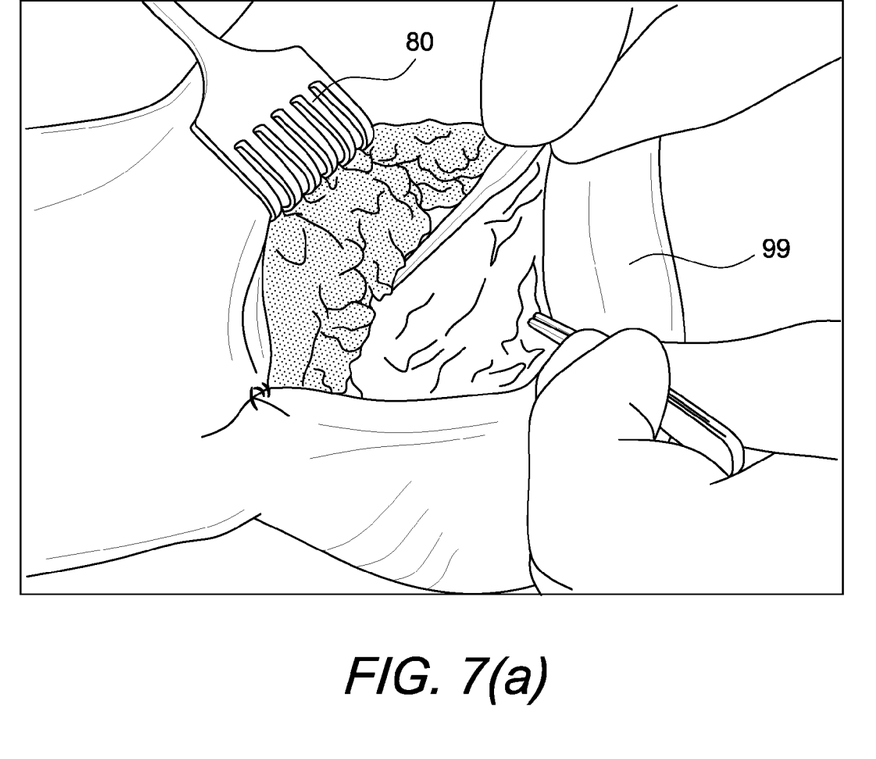

FIGS. 6, 7 and 7a illustrate the formation of an incision 98 on the lateral side of ankle 99 and preparation of the bone (using a retractors 80 such as a Hohmann retractor 80, for example). Incision 98 is slightly curved, i.e., formed at an angle of about 90 degrees (as compared to the more straight-line incisions of the prior art) to avoid the skin scar over the osteotomy site and to better conform to the structural characteristics of the plate to be inserted.

Figure 8:
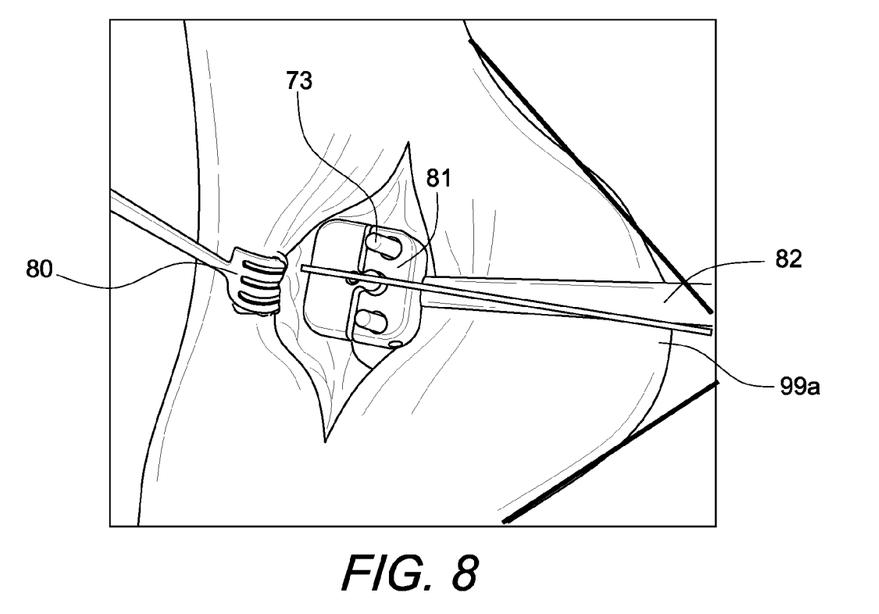
Figure 9:
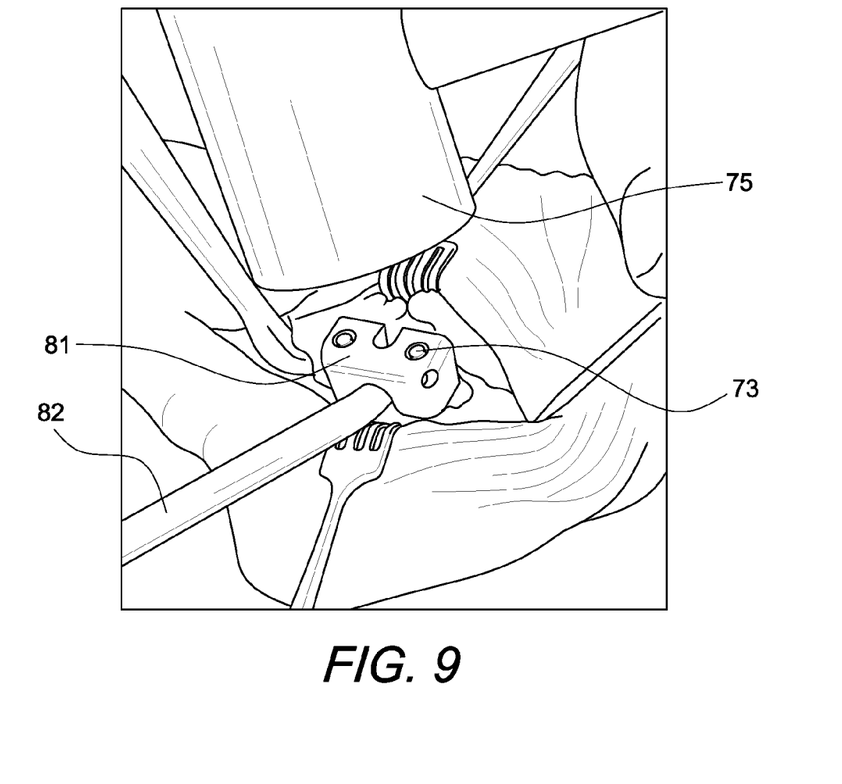

FIGS. 8 and 9 illustrate the placement of a saw template 81 (with handle 82 pointing to heel tip 99a) and the removal of the template (mating part) and the placement of the pins 73 (FIGS. 8 and 9) into bone (calcaneus) using a hammer 75 (FIG. 9), for example. Saw template 81 is provided with a plain surface needed for placement of the sawcut (explained below) and is pinned to bone 99 with two single pins 73. As detailed below, the screw hole orientation of the plate 100 is angled to its planes, which requires: angulation of the saw template pins 73 (when completely seated, the pins 73 reach about 3 mm into the bone); and a locking drill guide perpendicular to the screw axis (i.e., requires angulation to the plate's planes and a recess in the plate that allows perpendicular mounting of the drill guide). Using this drill guide, the same 3 mm hole is enlarged by K-wires, for example, and drills that allow insertion of screws in a standard fashion.

Figure 10:
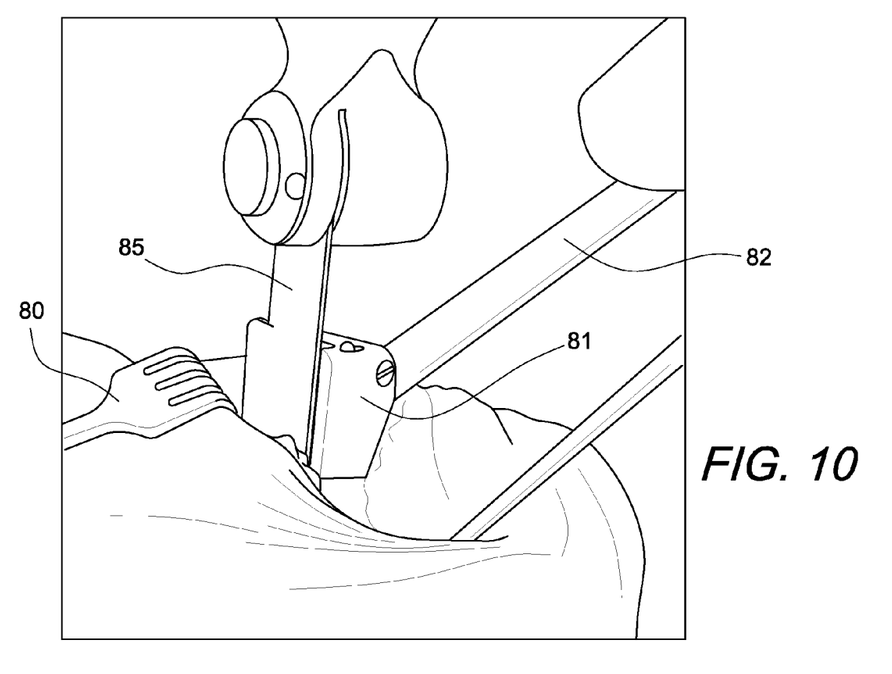
Figure 11:
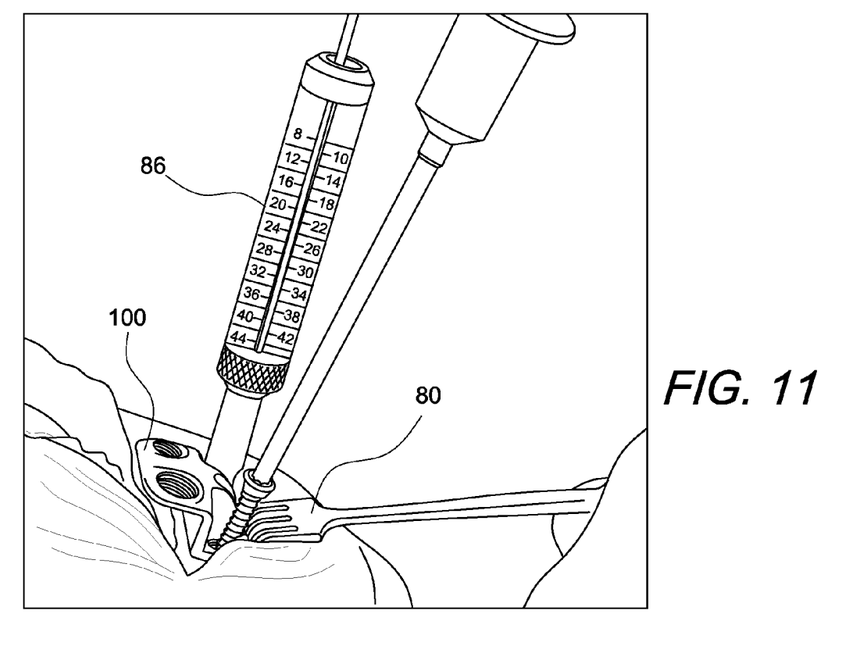

FIGS. 10 and 11 illustrate sawcut 85 along the template edge through the calcaneus with the Hohmann retractor 80 to protect blood vessels and/or nerves on the medial side (FIG. 10). FIG. 11 illustrates removal of the template 81 (using Hohmann retractors as a lever) and the placement of K-wires into prepinned holes. The locking guide allows drilling/used for orientation of screw angulation. Also shown in FIG. 11 is the evaluation of the screw length with a depth measuring device 86.

Figure 12:
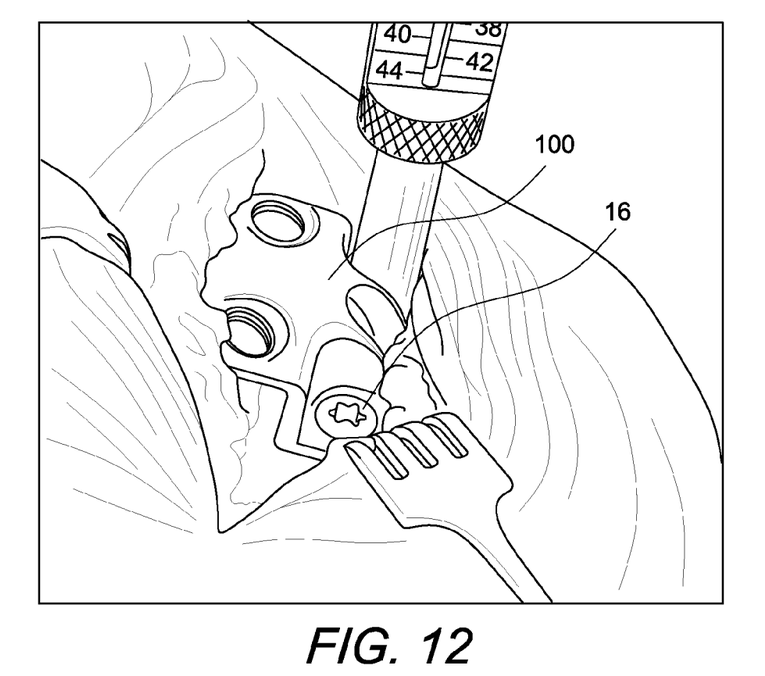
Figure 13:
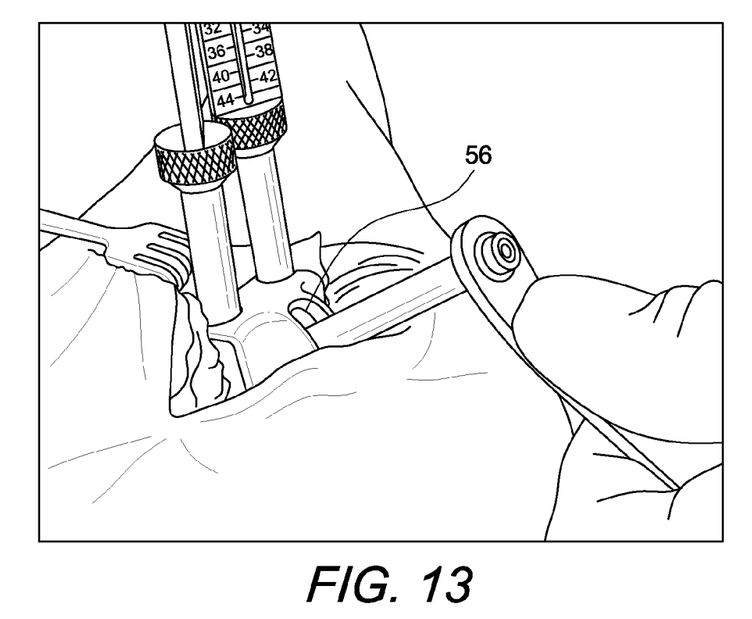

FIGS. 12 and 13 illustrate insertion/placement of the locking screws 16 in the standard fashion (distal part of calcaneus (2×)) and positioning of the plate 100 in the final position (distal part to be pushed down) using a retractor (for example, a Cobra retractor) and mounted drill guides. Also shown in FIG. 13 is predrilling of the compression screw hole 56 (at an angulation of about 45 degrees to bone at lower end of sliding hole).

Figure 14:
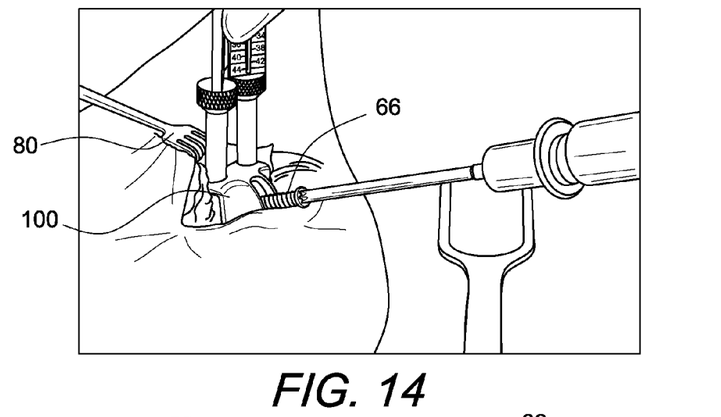
Figure 15A:
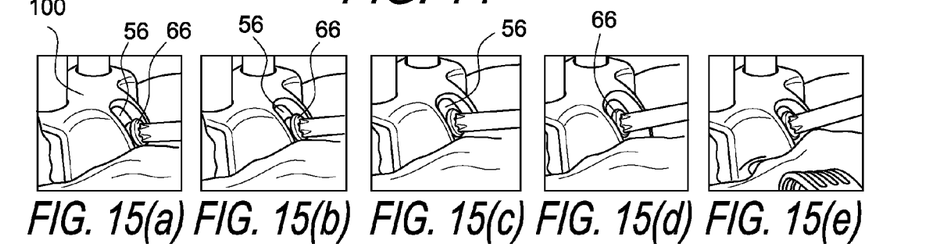
Figure 16A:
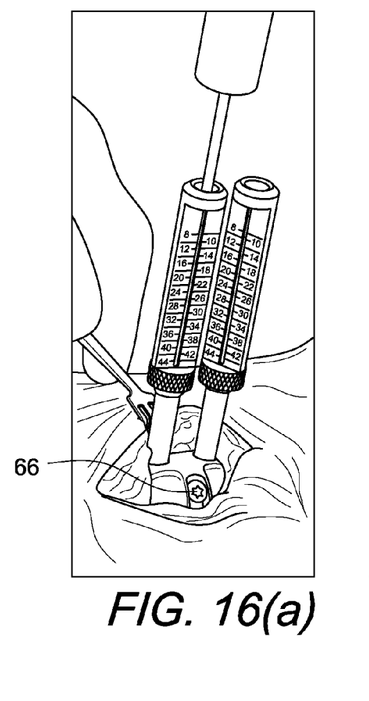
Figure 16B:
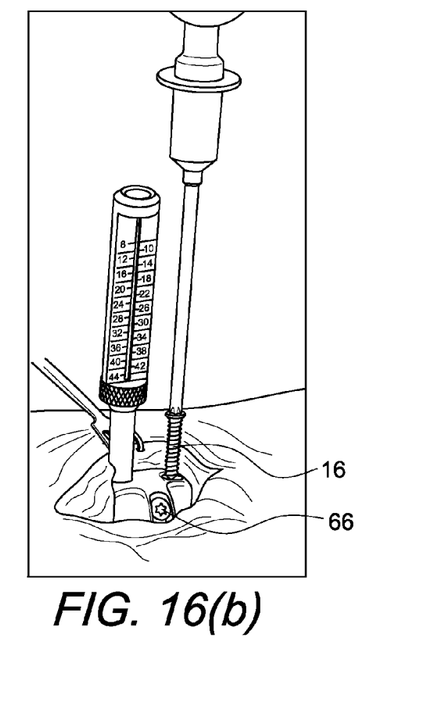

FIGS. 14-16 illustrate insertion of the compression screw 66 and the advancement of the screw 66 in the compression hole 56 (FIGS. 15(a)-(e)). FIG. 14 and FIGS. 15(a)-(e) show the placement of the compression hole with the screw head sliding up (from FIG. 15(a) to FIG. 15(e)), adding compression to the counter cortex. FIGS. 15(a)-(e) illustrate the compression hole sliding for step plate 100, shown at various stages of compression sliding. FIG. 16 illustrates predrilling/measuring/insertion of proximal screws 16 in a standard fashion.

Figure 17:
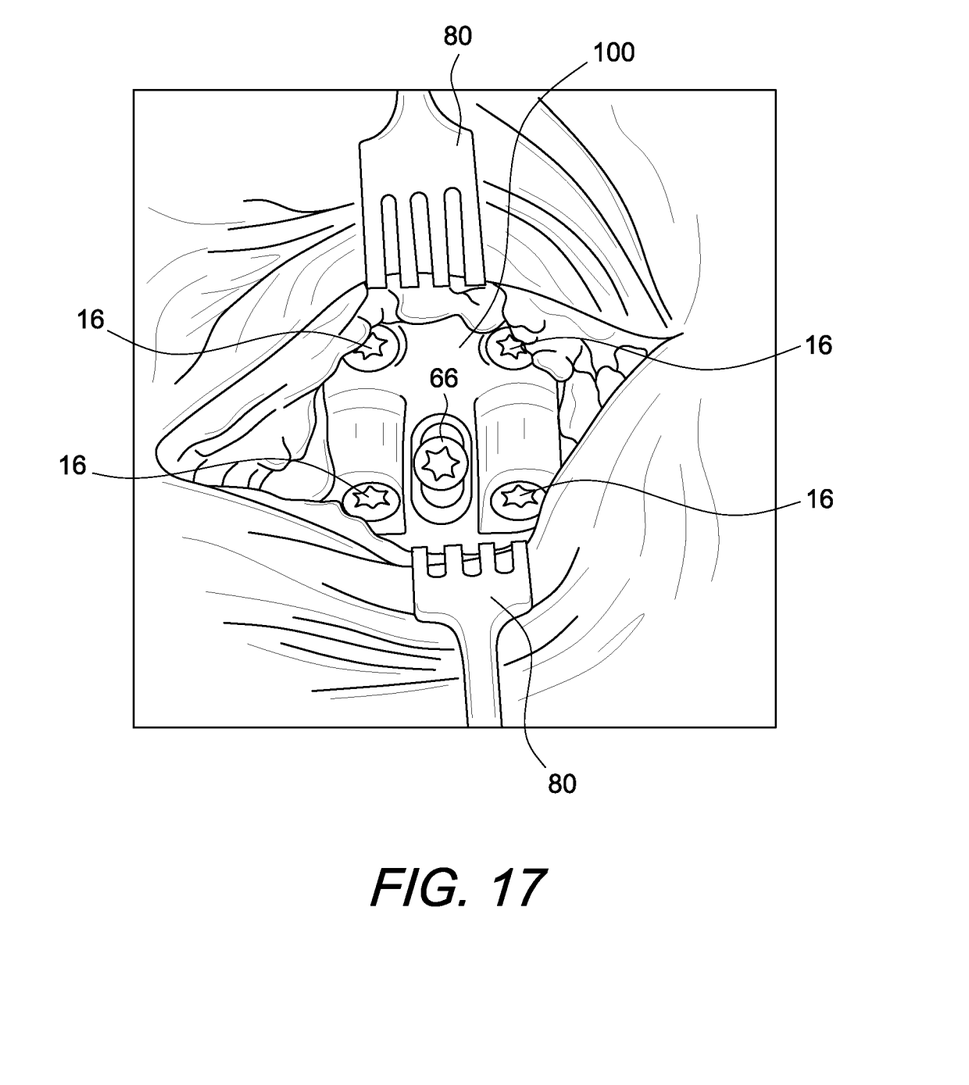

FIG. 17 illustrates plate 100 fully seated. Suturing of the surgical site may follow.

FIGS. 18-25 (Lateral Shift—Showing Only Differences Relative to the Medial Shift Approach)

Figure 18:
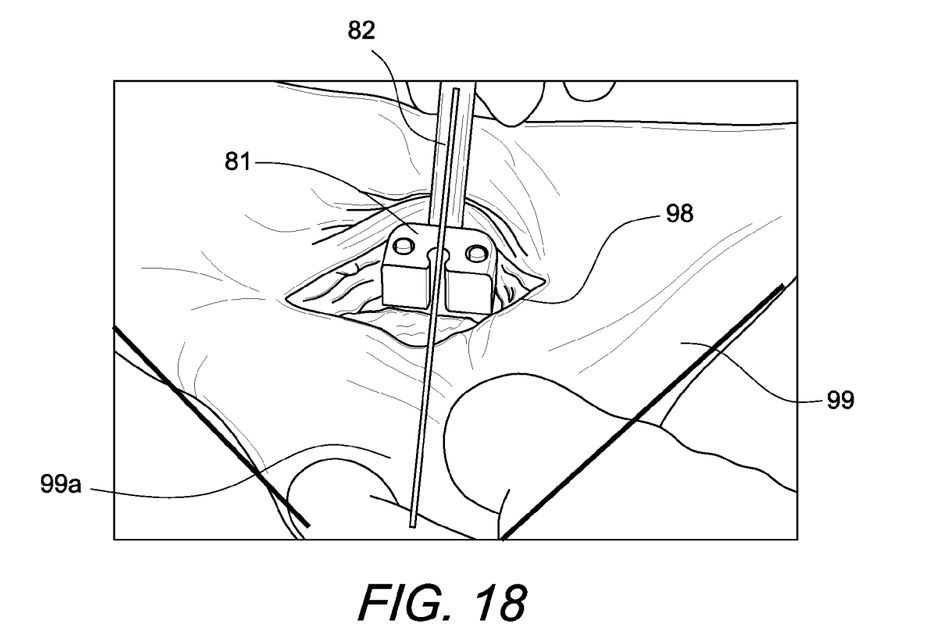
FIGS. 18-25 illustrate another sequence of steps of a calcaneal fracture treatment (lateral shift approach) with the correction osteotomy plate of the present invention.
Figure 19:
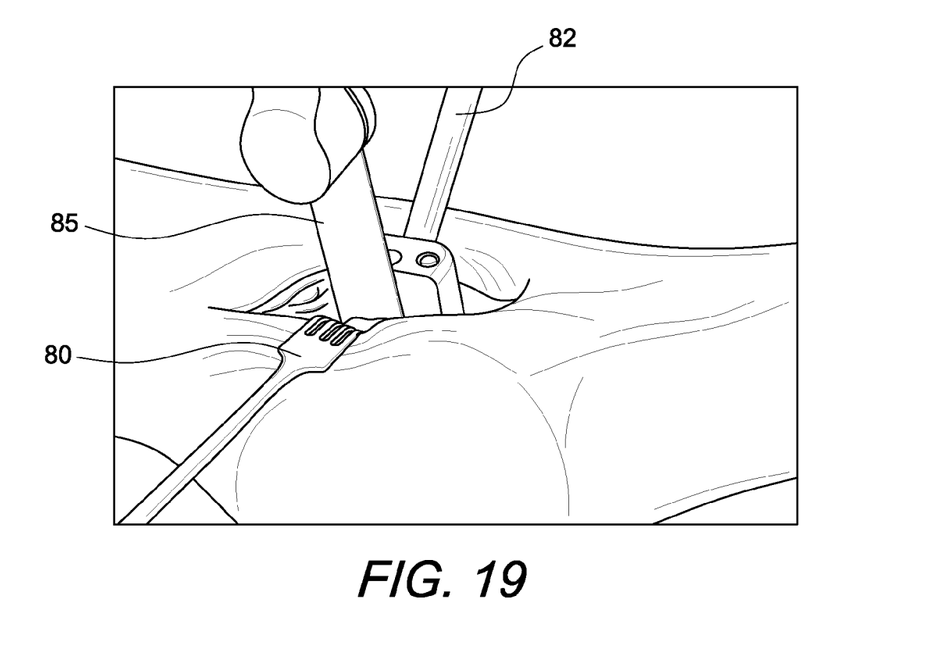

FIGS. 18 and 19 illustrate the insertion of the template 81 with handle 82 pointing toward the heel tip 99a and the placement of the sawcut 85 along the template edge. Incision 98 is slightly curved, i.e., formed at an angle of about 90 degrees (as compared to the more straight-line incisions of the prior art) to avoid the skin scar over the osteotomy site and to better conform to the structural characteristics of the plate 100 to be inserted.

Figure 20:
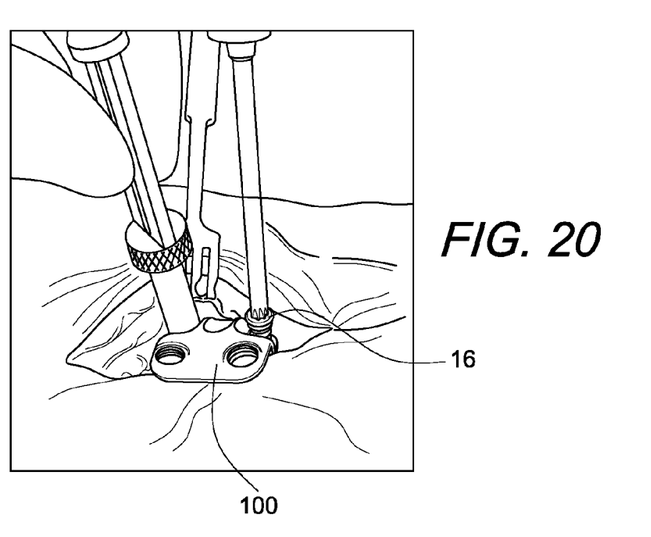
Figure 21:
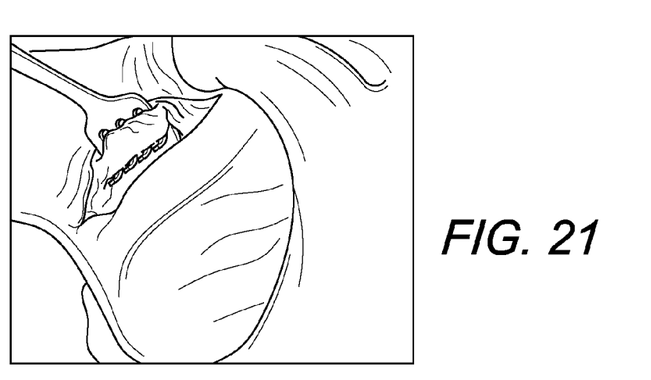
Figure 22:
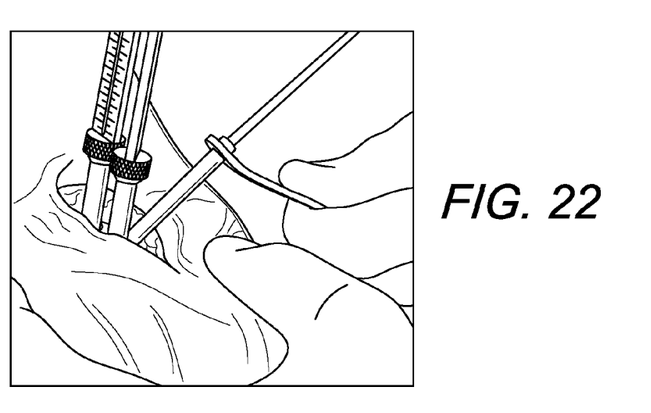
Figure 23A:
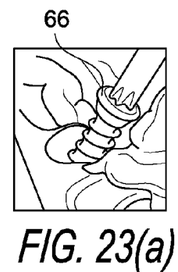
Figure 23B:
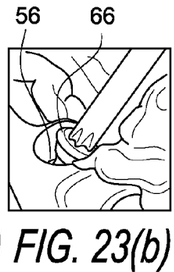
Figure 23C:
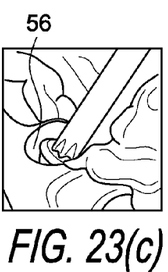
Figure 23D:
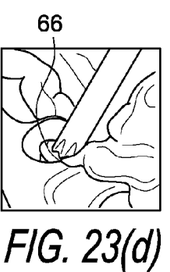
Figure 23E:
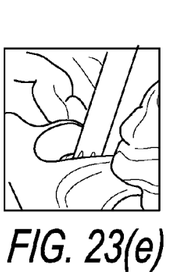

FIGS. 20-22 illustrate placement of the proximal screws 16 in the standard fashion and the final positioning of the plate 100 (distal part to be pushed down) using a retractor (for example, a Cobra retractor) and mounted drill guides (FIG. 21). FIG. 22 shows predrilling of the compression screw hole 56 towards the heel tip and the evaluation of the length of the compression screw 66 (with a depth measuring device).

FIGS. 23(*a*)-(*e*) show the insertion/sliding of the screw 66 in the compression hole 56 (at various stages of compression sliding). FIGS. 23(*a*)-(*e*) show the placement of the compression hole with the screw head sliding up (from FIG. 23(*a*) to FIG. 23(*e*)), adding compression to the counter cortex.

Figure 24:
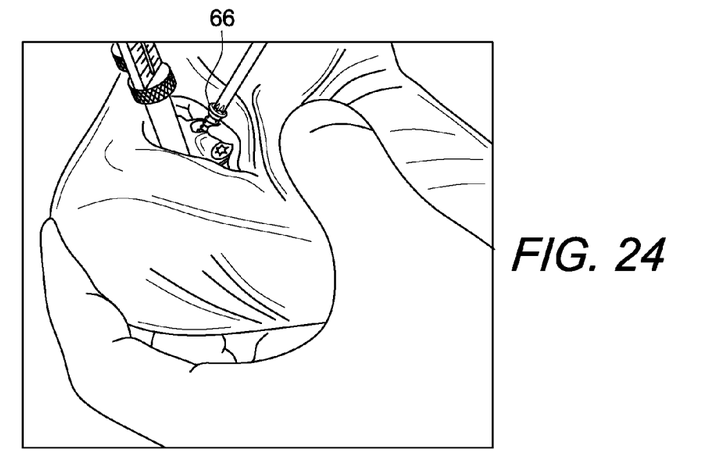
Figure 25:
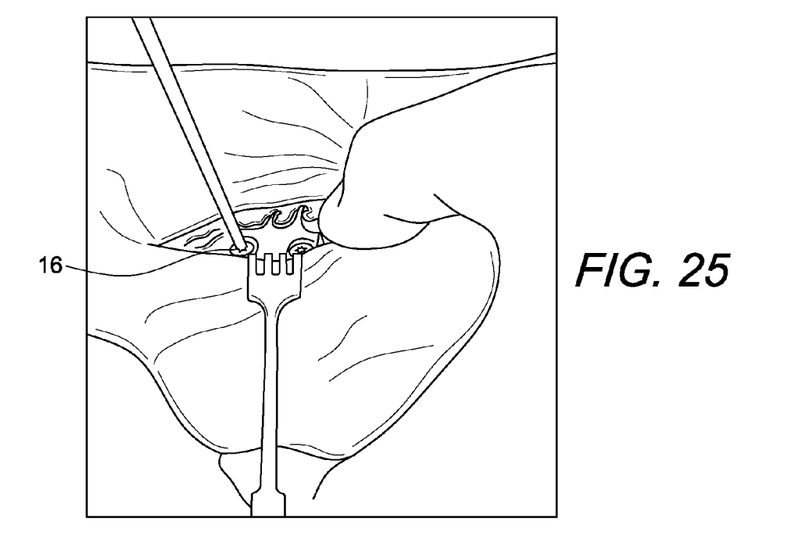

FIGS. 24 and 25 illustrate the insertion/placement of the compression screw (FIG. 24) and insertion of the distal screws 16 in a standard fashion (FIG. 25).

The calcaneus step plate of the present invention provides the possibility of adding compression to the medial side of the calcaneus and of the osteotomy. The calcaneus step plate with the unique sliding mechanism may be employed to address adult flatfoot, to correct hindfoot valgus after recurrent pronation trauma and deltoid ligament insufficiency, and to correct a misaligned ankle with deformity, among many others.

The calcaneus step plate of the present invention is a correction osteotomy plate that confers improved remodeling according to the lateral wall of the calcaneus. The plate is suited to the mechanical and biological characteristics of intra-articular calcaneal fracture repairs, with improved results (i.e., with reduced irritation of soft tissues and tendons, and decreased number of late complications necessitating corrective procedures occurring subsequent to the fracture treatment).

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A calcaneus step bone plate, comprising:
   a first plate section and a second plate section extending about parallel to the first plate section;
   an intermediate plate connecting the first and second plate sections and extending about perpendicular to the first and second plate sections; and
   an arcuate protrusion extending away from the intermediate plate and in a direction about perpendicular to the intermediate plate, the arcuate protrusion comprising a truncated passage or through-hole for receiving a compression fixation device, the through-hole located about a middle of the arcuate protrusion and defining a sliding mechanism to allow the compression fixation device to both slide and rotate relative to the arcuate protrusion to achieve compression on a counter calcaneus cortex.

2. The bone plate of claim 1, wherein the arcuate protrusion is integral to the intermediate plate.

3. The bone plate of claim 1, wherein the compression fixation device is a compression screw.

4. The bone plate of claim 1, wherein the truncated passage of the center sliding mechanism includes an inner outlet opening and an opposing outer inlet opening, wherein a cross section of the inner outlet opening is smaller than a cross section of the outer inlet opening.

5. The bone plate of claim 1, wherein one of the first and second plate sections has a wedged profile.

6. The bone plate of claim 1, wherein each of the first and second plate sections is provided with a plurality of apertures passing through the first and second plate sections.

7. The bone plate of claim 6, wherein each of the apertures accommodates a fixation device.

8. The bone plate of claim 6, wherein each of the apertures is located in a corner of the first and second plate sections.

9. The bone plate of claim 1, wherein the plate has a stepped configuration.

10. A calcaneus step plate assembly for engagement with a calcaneus bone, comprising:
    a calcaneus step plate positioned proximate to the calcaneus, the calcaneus step plate comprising:
    a first plate and a second plate extending about parallel to the first plate;
    an intermediate wall connecting the first and second plates and extending about perpendicular to the first and second plates, so that the first and second plates are symmetrically located relative to the intermediate wall and opposite to each other; and
    an arcuate protrusion extending away from the intermediate wall and in a direction about perpendicular to the intermediate wall;
    a compression fixation device for engagement with the through-hole of the truncated passage and with the calcaneus; and
    at least one fixation device for securing the first and second plates to the calcaneus, wherein the arcuate protrusion includes a truncated passage or through-hole, the through-hole located about a middle of the arcuate protrusion and defining a sliding mechanism to allow the compression fixation device to both slide and rotate relative to the arcuate protrusion to achieve compression on a counter calcaneus cortex.

11. The plate assembly of claim 10, wherein one of the first and second plates has a uniform height and the other one of the first and second plates has a gradual height with a wedged profile.

12. The plate assembly of claim 10, wherein the compression fixation device is a screw that slides and rotates within the through-hole.

13. A method of calcaneus repair, comprising the steps of:
    providing a calcaneus step plate having a body with a first plate and a second plate extending about parallel to the first plate; an intermediate plate connecting the first and second plates and extending about perpendicular to the first and second plates; and an arcuate protrusion extending away from the intermediate plate and in a direction about perpendicular to the intermediate plate;
    positioning the calcaneus step plate proximal to the calcaneus; and
    securing the calcaneus step plate to the calcaneus by providing a compression fixation device through a through-hole in the arcuate protrusion, wherein the arcuate protrusion is provided with a center sliding mechanism located at about a middle of the protrusion, to allow the compression fixation device to both slide and rotate relative to the arcuate protrusion to achieve compression on a counter calcaneus cortex.

14. The method of claim 13, wherein the step of securing the calcaneus step plate to the calcaneus further comprises the steps of:
    providing a pair of through-holes through each of the first and second plates; and
    securing a fixation device through each of the through-holes of the first and second plates, and into the calcaneus.

15. The method of claim 14, wherein the fixation device is selected from the group consisting of a washer, a screw and an anchor.

* * * * *